(12) United States Patent
Meroueh

(10) Patent No.: US 9,376,406 B2
(45) Date of Patent: Jun. 28, 2016

(54) UPAR-UPA INTERACTION INHIBITORS AND METHODS FOR TREATING CANCER

(75) Inventor: Samy Meroueh, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 24 days.

(21) Appl. No.: 14/002,814

(22) PCT Filed: Mar. 2, 2012

(86) PCT No.: PCT/US2012/027498
§ 371 (c)(1),
(2), (4) Date: Sep. 3, 2013

(87) PCT Pub. No.: WO2012/119079
PCT Pub. Date: Sep. 7, 2012

(65) Prior Publication Data
US 2013/0338144 A1    Dec. 19, 2013

Related U.S. Application Data

(60) Provisional application No. 61/448,779, filed on Mar. 3, 2011.

(51) Int. Cl.
*C07D 261/20* (2006.01)
*C07D 413/04* (2006.01)
*G01N 33/50* (2006.01)

(52) U.S. Cl.
CPC ............ *C07D 261/20* (2013.01); *C07D 413/04* (2013.01); *G01N 33/5008* (2013.01)

(58) Field of Classification Search
CPC .................................................. C07D 261/20
See application file for complete search history.

(56) References Cited

U.S. PATENT DOCUMENTS

| 4,556,654 | A | 12/1985 | Showalter et al. |
| 4,672,129 | A | 6/1987 | Beylin et al. |
| 5,079,358 | A | 1/1992 | Sugaya et al. |
| 5,393,886 | A | 2/1995 | Zhang et al. |
| 6,194,422 | B1 | 2/2001 | Caruso et al. |
| 7,119,114 | B1 | 10/2006 | Bennett et al. |

FOREIGN PATENT DOCUMENTS

WO    WO 2010077680 A2 *  7/2010

OTHER PUBLICATIONS

Dunbar, S., et al. "Cancer treatment with inhibitors of urokinase-type plasminogen activator and plasmin." Expert. Op. Invest. Drugs. (2000), vol. 9(9), pp. 2085-2092.*
Mani, T., et al. "Small-molecule inhibition of the uPAR-uPA interaction: Synthesis, Biochemical, cellular, in vivo pharmacokinetics and efficacy studies in breast cancer metastasis." Bioorganic and Medicinal Chemistry. (2013), vol. 21, pp. 2145-2155.*
Stanford Medicine. "Chemotherapy Drugs and Side Effects." © 2014. Available from: <http://cancer.stanford.edu/information/cancerTreatment/methods/chemotherapy.html >.*
"Realistic Rodents? Debate Grows Over New Mouse Models of Cancer." J. Nat'l Cancer Inst. (2006), vol. 98, No. 17, pp. 1176-1178.*
PCT International Search Report and Written Opinion completed by the ISA/US on May 22, 2012 and issued in connection with PCT/US2012/07498.
Baguley, et al. "Antitumour Activity of Substituted 9-Anilinoacridinescomparison of In Vivo and In Vitro Testing Systems" Europ. J. Cancer 17, 671 (1981) Abstract.
Erlichman, et al. "Phase I Pharmacokinetic and Pharmacodynamic Study of a New Anthrapyrazole" CI-937 (DUP937). Cancer Res 1991; 51:6317-6322. Abstract.
Fry. "Biochemical Pharmacology of Anthracenediones and Anthrapyrazoles" Pharmac. Ther. vol. 52, pp. 109-125, 1991 Abstract.
Loadman, et al. "Spearation Methods for Anthraquinone Related Anti-Cancer Drugs" Journal of Chromatography B, 764 (2001) 193-206 p. 197, col. 2, para 2.
Leopold, et al. "Anthrapyrazoles, a New Class of Intercalating Agents with High-Level, Broad Spectrum Activity Against Murine Tumors" Cancer Res. 1985; 45: 5532-5539. Abstract.

* cited by examiner

*Primary Examiner* — Noble Jarrell
*Assistant Examiner* — John S Kenyon
(74) *Attorney, Agent, or Firm* — Barnes & Thornburg LLP

(57) ABSTRACT

The invention described herein pertains to compounds, compositions and formulations comprising the compounds, and methods for use of the compounds, compositions and/or formulations in the treatment of diseases responsive to the inhibition of uPAR-uPA interactions, such as cancer.

10 Claims, 5 Drawing Sheets

SEQUENCE LISTING

<160> NUMBER OF SEQ ID NOS: 1

<210> SEQ ID NO 1
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term fluorescein

<400> SEQUENCE: 1

Cys Leu Asn Gly Gly Thr Cys Val Ser Asn Lys Tyr Phe Ser Asn Ile
1               5                   10                  15

His Trp Cys Asn
            20
```

UPAR-UPA INTERACTION INHIBITORS AND METHODS FOR TREATING CANCER

CROSS REFERENCE TO RELATED APPLICATIONS

This application is a U.S. national counterpart application of International Application No. PCT/US2012/027498 filed Mar. 2, 2012, which claims the benefit of U.S. Provisional Patent Application No. 61/448,779 filed Mar. 3, 2011. The entire disclosures of PCT/US2012/027498 and U.S. Ser. No. 61/448,779 are hereby incorporated by reference.

STATEMENT REGARDING FEDERALLY SPONSORED RESEARCH OR DEVELOPMENT

This invention was made with government support under CA135380 awarded by the National Institutes of Health. The U.S. Government has certain rights in the invention.

INCORPORATION BY REFERENCE OF MATERIAL SUBMITTED ELECTRONICALLY

Incorporated by reference in its entirety is a computer-readable amino acid sequence listing submitted concurrently herewith and identified as follows: One 667 bytes (Text) file named "SL_220498.txt" created on 3 Sep. 2013.

TECHNICAL FIELD

The invention described herein pertains to compounds, compositions and formulations comprising the compounds, and methods for use of the compounds, compositions and/or formulations in the treatment of diseases responsive to the inhibition of uPAR-uPA interactions, such as cancer.

BACKGROUND AND SUMMARY OF THE INVENTION

The interaction of the glycosylphosphatidylinositol (GPI)-anchored cell-surface urokinase receptor (uPAR) and its serine protease ligand urokinase-type plasminogen activator (uPA) is believed to be implicated in nearly every step of tumor formation and progression, including tumorigenesis (1. Shapiro et al. (1997) Urokinase-type plasminogen activator-deficient mice are predisposed to staphylococcal botryomycosis, pleuritis, and effacement of lymphoid follicles. The American journal of pathology 150(1):359-369; the foregoing publication, and each additional publication cited herein, is incorporated herein by reference in its entirety), cell proliferation (2. Gandhari et al. (2006) Urokinase-type plasminogen activator induces proliferation in breast cancer cells. International Journal of Oncology 28(6):1463-1470; 3. Liang et al. (2008) RNAi-mediated downregulation of urokinase plasminogen activator receptor inhibits proliferation, adhesion, migration and invasion in oral cancer cells. Oral Oncol.; 4. Kondraganti et al. (2006) RNAi-mediated downregulation of urokinase plasminogen activator and its receptor in human meningioma cells inhibits tumor invasion and growth. Int J Oncol 28(6):1353-1360), cell migration (5. Prager et al. (2004) Vascular endothelial growth factor receptor-2-induced initial endothelial cell migration depends on the presence of the urokinase receptor. Circ Res 94(12):1562-1570; 6. Schiller et al. (2009) Mannose 6-phosphate/insulin-like growth factor 2 receptor limits cell invasion by controlling alphaVbeta3 integrin expression and proteolytic processing of urokinase-type plasminogen activator receptor. Molecular biology of the cell 20(3):745-756), adhesion (3; 7. Andreasen et al. (1997) The urokinase-type plasminogen activator system in cancer metastasis: A review. Int J Cancer 72(1):1-22), angiogenesis (8. Mignatti & Rifkin (1996) Plasminogen activators and matrix metalloproteinases in angiogenesis. Enzyme & protein 49(1-3):117-137; 9. Rabbani & Mazar (2001) The role of the plasminogen activation system in angiogenesis and metastasis. Surgical oncology clinics of North America 10(2):393-415, x), and invasion (3, 4, 10. Subramanian et al. (2006) siRNA-mediated simultaneous downregulation of uPA and its receptor inhibits angiogenesis and invasiveness triggering apoptosis in breast cancer cells. International Journal of Oncology 28(4):831-839; 11. Kunigal et al. (2007) RNAi-mediated downregulation of urokinase plasminogen activator receptor and matrix metalloprotease-9 in human breast cancer cells results in decreased tumor invasion, angiogenesis and growth. International journal of cancer 121(10):2307-2316). The uPAR•uPA complex formation has been reported to enhance pericellular proteolysis through activation of plasminogen (7), culminating in the active degradation of extracellular matrix (ECM) components. Whereas uPAR is believed to have no inherent signaling capability, it has been reported that the uPAR•uPA complex promotes signaling by actively associating to cell surface receptors such as integrins (12. Wei et al. (1996) Regulation of integrin function by the urokinase receptor. Science 273(5281):1551-1555), receptor tyrosine kinases (RTKs) (13. Kiyan et al. (2005) Urokinase-induced signaling in human vascular smooth muscle cells is mediated by PDGFR-beta. Embo J 24(10):1787-1797; 14. Liu et al. (2002) EGFR is a transducer of the urokinase receptor initiated signal that is required for in vivo growth of a human carcinoma. Cancer cell 1(5):445-457), and G-protein coupled receptors (GPCRs) (15. Resnati et al. (2002) The fibrinolytic receptor for urokinase activates the G protein-coupled chemotactic receptor FPRL1/LXA4R. P Natl Acad Sci USA 99(3):1359-1364). Furthermore, it is believed that uPAR binding to vitronectin components may indicate interactions that extend beyond the cell surface to engage the microenvironment and further promote metastasis.

Compounds capable of disrupting such uPAR-uPA complexes have not been reported (16. Chen et al. (2009) Challenges for Drug Discovery—A Case Study of Urokinase Receptor Inhibition. Combinatorial chemistry & high throughput screening 12(10):961-967). Instead, efforts concentrating on inhibiting the enzymatic activity of uPA have been reported, which may neglect the signaling capabilities of the receptor. It has been reported that the uPAR•uPA complex poses the same challenges that have plagued efforts to inhibit protein-protein interactions with small molecules in the past (17. Arkin & Wells (2004) Small-molecule inhibitors of protein-protein interactions: progressing towards the dream. Nature reviews 3(4):301-317), which include a tight interaction (18. Ploug & Ellis (1994) Structure-function relationships in the receptor for urokinase-type plasminogen activator. Comparison to other members of the Ly-6 family and snake venom alpha-neurotoxins. Febs Lett 349(2):163-168; 19. Gardsvoll et al. (2006) Characterization of the functional epitope on the urokinase receptor. Complete alanine scanning mutagenesis supplemented by chemical cross-linking. The Journal of biological chemistry 281(28):19260-19272), a large interaction surface estimated at 1,318 Å$^2$ (20. Huai et al. (2006) Structure of human urokinase plasminogen activator in complex with its receptor. Science 311(5761):656-659), and inherent flexibility of the target (21. Wells & McClendon (2007) Reaching for high-hanging fruit in drug discovery at protein-protein interfaces. Nature 450(7172):1001-1009).

There exists a need for compounds that are capable of disrupting such uPAR-uPA complexes in the treatment of disease. Without being bound by theory, it is believed herein that small molecules that disrupt hot-spot interactions may be particularly useful for inhibiting protein-protein interactions, such as are present in uPAR-uPA complexes (22. Cerchietti et al. (2010) A Small-Molecule Inhibitor of BCL6 Kills DLBCL Cells In Vitro and In Vivo. Cancer cell 17(4):400-411; 23. Vassilev et al. (2004) In vivo activation of the p53 pathway by small-molecule antagonists of MDM2. Science 303(5659): 844-848; 24. Christ et al. (2010) Rational design of small-molecule inhibitors of the LEDGF/p75-integrase interaction and HIV replication. Nature Chemical Biology 6(6):442-448; 25. Oltersdorf et al. (2005) An inhibitor of Bcl-2 family proteins induces regression of solid tumours. Nature 435 (7042):677-681; 26. Roehrl et al. (2004) Selective inhibition of calcineurin-NFAT signaling by blocking protein-protein interaction with small organic molecules. Proceedings of the National Academy of Sciences of the United States of America 101(20):7554-7559).

Described herein is a computational approach for screening and selecting molecules, including small molecules, that inhibit the uPAR•uPA interaction. Without being bound by theory, it is believed herein that targeting unproductive alternative conformations of uPAR concomitant with disrupting hot-spot interactions at the complex interface (19) may lead to more effective inhibitors of the high-affinity interaction. It is understood herein that it may be advantageous to distinguish those molecules that merely bind to a target, which may be initially identified, from those molecules that are capable of displacing the full protein-protein interaction. Also described herein is the targeting of representative conformers collected from MD simulations by virtual screening of large libraries of compounds. The process includes selecting compounds from the library screen and initially assessing each for activity in a fluorescence polarization assay then in a microtiter-based ELISA. Also described herein is immunofluorescence imaging in tumor cells, which establishes that disruption of uPAR•uPA is also observed in tumor cells. The effect of inhibitors in blocking processes critical in tumor invasion, migration and adhesion of tumor cells, including highly aggressive breast MDA-MB-231 and lung H1299, in cell culture is also described herein.

In one embodiment, described herein are compounds that inhibit interactions of the urokinase receptor, a protein whose interactions are widely believed to promote tumor invasion and metastasis.

In another embodiment, compounds described herein bind at the uPAR/uPA interface, thereby inhibiting the binding of uPA to uPAR and blocking activation of uPA at the cell surface. In another embodiment, compounds described herein that inhibit the uPAR-uPA interaction in vitro. In another embodiment, compounds described herein inhibit the uPAR-uPA interaction in highly aggressive breast and lung tumor cells. In another embodiment, compounds described herein show inhibition of lung and breast cancer invasion, which is a process that drives cancer metastasis in patients. In another embodiment, compounds described herein bind to uPAR on invading cells and block binding of uPA, thus preventing invading cells from invading normal cells, and also preventing cancer cells from migrating.

It has been discovered herein that the compounds described herein inhibit the uPAR-uPA protein-protein interaction. In one embodiment, compounds described herein are useful as chemical probes for this interaction. In another embodiment, compounds described herein are useful as leads for the development of therapeutic agents to block metastasis in the clinic. In another embodiment, compounds described herein are useful in the treatment of cancer.

In one illustrative embodiment of the invention, compounds of the following formula are described herein:

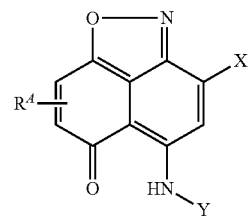

or pharmaceutically acceptable salts thereof, wherein $R^A$, X, and Y are as defined below in the various illustrative embodiments herein.

In addition, various genera and subgenera of each of $R^A$, X, and Y are described herein. It is to be understood that all possible combinations of the various genera and subgenera of each of $R^A$, X, and Y described herein represent additional illustrative embodiments of compounds of the invention described herein. It is to be further understood that each of those additional illustrative embodiments of compounds may be used in any of the compositions, methods, and/or uses described herein.

In another embodiment, pharmaceutical compositions containing one or more of the compounds are also described herein. In one aspect, the compositions include a therapeutically effective amount of the one or more compounds for treating a patient with cancer. It is to be understood that the compositions may include other components and/or ingredients, including, but not limited to, other therapeutically active compounds, and/or one or more carriers, diluents, excipients, and the like, and all combinations of the foregoing.

In another embodiment, methods for using the compounds and pharmaceutical compositions for treating patients with cancer are also described herein. In one aspect, the methods include the step of administering one or more of the compounds and/or compositions described herein to a patient with cancer. In another aspect, the methods include administering a therapeutically effective amount of the one or more compounds and/or compositions described herein for treating patients with cancer.

In another embodiment, uses of the compounds and compositions in the manufacture of a medicament for treating patients with cancer are also described herein. In one aspect, the medicaments include a therapeutically effective amount of the one or more compounds and/or compositions for treating a patient with cancer.

It is appreciated herein that the compounds described herein may be used alone or in combination with other compounds useful for treating cancer, including those compounds that may be therapeutically effective by the same or different modes of action. In addition, it is appreciated herein that the compounds described herein may be used in combination with other compounds that are administered to treat other symptoms of cancer.

DETAILED DESCRIPTION

Figure 1A:
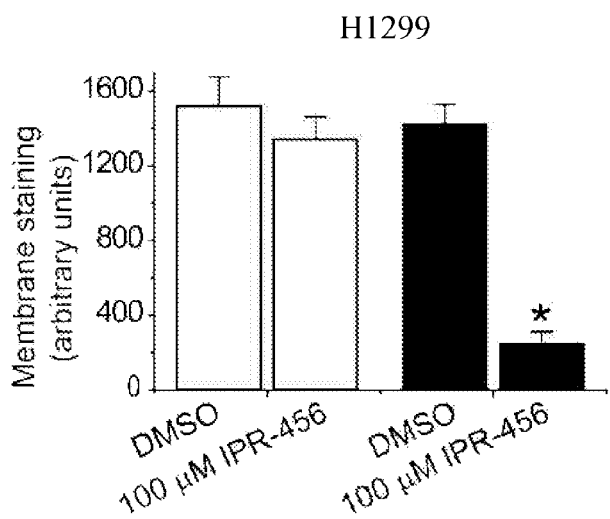
FIG. 1 shows membrane staining of (a) H1299 cells, and (b) MDA-MB-231 cells.

In one embodiment, described herein is a pharmaceutical composition comprising a therapeutically effective amount of one or more compounds of the formula

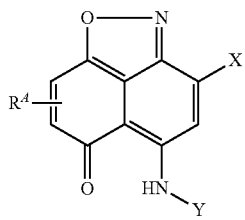

or a pharmaceutically acceptable salt thereof, wherein:
X is amino or a derivative thereof, or an optionally substituted nitrogen-containing heterocycle attached at nitrogen;
Y is optionally substituted aryl or optionally substituted heteroaryl; and
$R^A$ represents two substituents, each independently selected from the group consisting of hydrogen, halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or $R^A$ is a fused aryl or heteroaryl ring, which is optionally substituted.

In another embodiment, described herein is the composition as in the above embodiment, further comprising one or more carriers, diluents, or excipients, or a combination thereof.

In another embodiment, described herein is the composition of any one of the above embodiments wherein the compound is of the formula

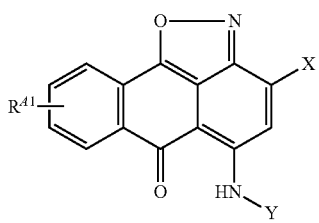

or a pharmaceutically acceptable salt thereof, wherein:
$R^{A1}$ represents four substituents, each independently selected from the group consisting of hydrogen, halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

In another embodiment, described herein is the composition of any one of the other embodiments herein, wherein Y is optionally substituted aryl or optionally substituted heteroaryl, substituted with a carboxylic acid, or derivative or analog thereof.

In another embodiment, described herein is the composition of any one of the other embodiments herein, wherein X is an optionally substituted nitrogen-containing heterocycle attached at nitrogen.

In another embodiment, described herein is a unit dose or unit dosage form for treating cancer, the unit dose or unit dosage form comprising a therapeutically effective amount of one or more compositions of any one of the other embodiments herein.

In another embodiment, described herein is a method for treating cancer in a patient, the method comprising the step of administering to the patient a therapeutically effective amount of one or more compositions of any one of the embodiments herein, one or more unit doses or unit dosage forms of any one of the embodiments herein, or a combination thereof.

In another embodiment, described herein is a method for imaging or diagnosing a population of pathogenic cells, the method comprising the steps of contacting the population with one or more compositions of any one of the embodiments herein, and measuring a signal from the population.

In another embodiment, described herein is the method as described above, wherein the signal is a fluorescence signal.

In another embodiment, described herein is the method as described in any of the above embodiments, wherein the measuring step includes determining the red shift of the fluorescent signal.

In another embodiment, described herein is the method as described in any of the above embodiments, wherein the compound makes an energetically positive interaction with one or more of the residues selected from the group consisting of L150, L155, L168, and R53 on uPAR.

In another embodiment, described herein is the method as described in any of the above embodiments, wherein the total of all interactions with uPAR is at least about −10 kcal/mol.

In another embodiment, described herein is the method as described in any of the above embodiments, wherein the total of all interactions with uPAR is at least about −12 kcal/mol.

In another embodiment, described herein is the method as described in any of the above embodiments, wherein the total of all interactions with uPAR is at least about −14 kcal/mol.

In another embodiment, described herein is the method as described in any of the above embodiments, wherein the interaction with L150 is less then about −2 kcal/mol.

In another embodiment, described herein is the method as described in any of the above embodiments, wherein the interaction with L150 is less then about −2.25 kcal/mol.

In another embodiment, described herein is the method as described in any of the above embodiments, wherein the interaction with L150 is less then about −2.5 kcal/mol.

In another embodiment, described herein is the method as described in any of the above embodiments, wherein the interaction with L168 is less then about −1 kcal/mol.

In another embodiment, described herein is the method as described in any of the above embodiments, wherein the compound makes an energetically positive interaction with R53 on uPAR.

In another embodiment, described herein is the method as described in any of the above embodiments, wherein the interaction with R53 is greater than that of GFD.

In another embodiment, described herein is the method as described in any of the above embodiments, wherein the interaction with R53 is less then about −2.5 kcal/mol.

In another embodiment, described herein is the method as described in any of the above embodiments, wherein the interaction with R53 is less then about −3 kcal/mol.

In another embodiment, described herein is the method as described in any of the above embodiments, wherein the interaction with R53 is less then about −4 kcal/mol.

In another embodiment, described herein is the method as described in any of the above embodiments, wherein the interaction with R53 is less then about −5 kcal/mol.

In another embodiment, described herein is a compound of the formula

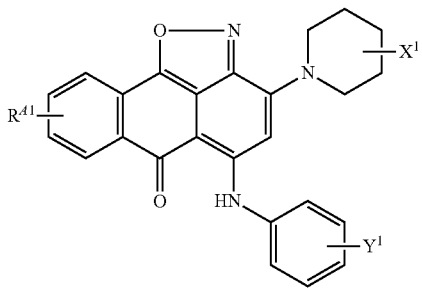

or a pharmaceutically acceptable salt thereof, wherein $X^1$ represents five substituents, each independently selected from the group consisting of hydrogen, halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $Y^1$ represents five substituents, each independently selected from the group consisting of hydrogen, halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

In another embodiment, each $X^1$ is selected from hydrogen and alkyl. In another embodiment, each $Y^1$ is selected from hydrogen and carboxylate or a derivative thereof. In another embodiment, $Y^1$ represents a single carboxylate or a derivative thereof.

In another embodiment, described herein is a compound of the formula

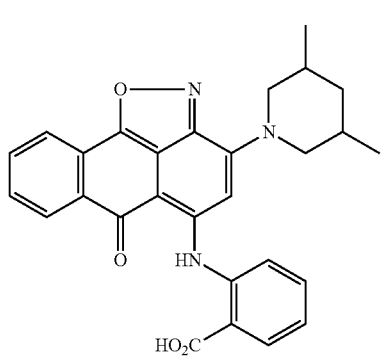 [SMILES: CC1CC(C)CN(c2cc(Nc3ccccc3C(=O)O)c3c4c(onc24)-c2ccccc2C3=O)C1]

also referred to herein as IPR-456, or a pharmaceutically acceptable salt thereof.

In another embodiment, described herein is a compound of the formula

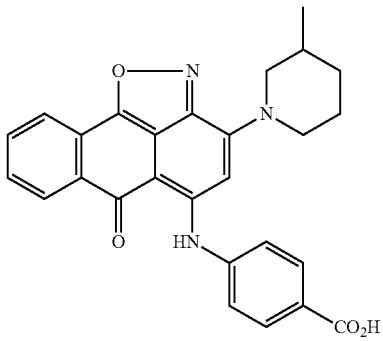 [SMILES: CC1CCCN(c2cc(Nc3ccc(C(=O)O)cc3)c3c4c(onc24)-c2ccccc2C3=O)C1]

also referred to herein as IPR-661, or a pharmaceutically acceptable salt thereof.

In another embodiment, described herein is a compound of the formula

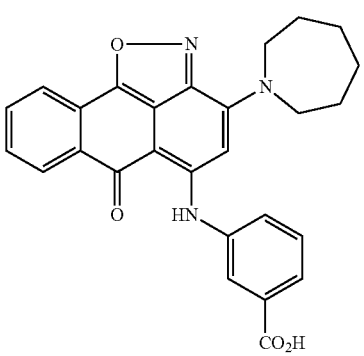

also referred to herein as IPR-803, or a pharmaceutically acceptable salt thereof.

In another embodiment, described herein is a compound of the formula

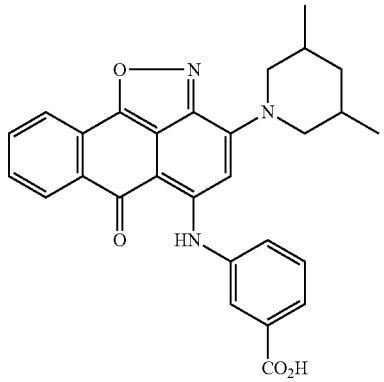

also referred to herein as IPR-824, or a pharmaceutically acceptable salt thereof.

The invention described herein is further illustrated by the embodiments of the following non-liming numbered clauses:

1. A pharmaceutical composition comprising a therapeutically effective amount for treating cancer of one or more compounds of the formula or a pharmaceutically acceptable salt thereof, wherein:

X is amino or a derivative thereof, or an optionally substituted nitrogen-containing heterocycle attached at nitrogen;

Y is optionally substituted aryl or optionally substituted heteroaryl; and $R^A$ represents two substituents, each independently selected from the group consisting of hydrogen, halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or $R^A$ is a fused aryl or heteroaryl, each of which is optionally substituted.

2. The composition of clause 1 wherein $R^A$ is a fused aryl or heteroaryl, each of which is optionally substituted.

3. The composition of clause 1 or 2 wherein $R^A$ is a fused optionally substituted aryl.

4. The composition of any one of the preceding clauses wherein the compound is of the formula or a pharmaceutically acceptable salt thereof, wherein:

$R^{A1}$ represents four substituents, each independently selected from the group consisting of hydrogen, halo, hydroxy, amino, thio, carboxylate or a derivative thereof, sulfinyl or a derivative thereof, sulfonyl or a derivative thereof, phosphinyl or a derivative thereof, or phosphonyl or a derivative thereof, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

5. The composition of any one of the preceding clauses wherein each $R^{A1}$ is hydrogen 6. The composition of any one of the preceding clauses The composition of any one of the preceding clauses wherein Y is substituted aryl or substituted heteroaryl.

7. The composition of any one of the preceding clauses wherein Y is substituted phenyl.

8. The composition of any one of the preceding clauses wherein Y is optionally substituted aryl or optionally substituted heteroaryl, substituted with a carboxylic acid, or derivative or analog thereof.

9. The composition of any one of the preceding clauses wherein Y is aryl substituted with a carboxylic acid, or derivative or analog thereof, or heteroaryl substituted with a carboxylic acid, or derivative or analog thereof.

10. The composition of any one of the preceding clauses wherein Y is phenyl substituted with a carboxylic acid.

11. The composition of any one of the preceding clauses wherein Y is an ortho benzoic acid radical, a meta benzoic acid radical, or a para benzoic acid radical.

12. The composition of any one of the preceding clauses wherein Y is an ortho or meta benzoic acid radical.

13. The composition of any one of the preceding clauses wherein X is an optionally substituted nitrogen-containing heterocycle attached at nitrogen.

14. The composition of any one of the preceding clauses where X is optionally substituted pyrrolidin-1-yl, piperidin-1-yl, or homopiperidin-1-yl.

15. The composition of any one of the preceding clauses where X is optionally substituted piperidin-1-yl.

16. The composition of any one of the preceding clauses where X is substituted piperidin-1-yl.

17. The composition of any one of the preceding clauses where X is alkyl substituted piperidin-1-yl.

18. The composition of any one of the preceding clauses where X is 3,5-dimethylpiperidin-1-yl or 3-methylpiperidin-1-yl.

19. The composition of any one of the preceding clauses where X is optionally substituted homopiperidin-1-yl.

20. The composition of any one of the preceding clauses where X is homopiperidin-1-yl.

21. The composition of any one of the preceding clauses-clause further comprising one or more carriers, diluents, or excipients, or a combination thereof.

22. A unit dose or unit dosage form for treating cancer, the unit dose or unit dosage form comprising a therapeutically effective amount of one or more compositions of any one of the preceding clauses for treating cancer.

23. A method for treating cancer in a patient, the method comprising the step of administering to the patient a therapeutically effective amount of one or more compositions of any one of the preceding clauses, one or more unit doses or unit dosage forms of any one of the preceding clauses, or a combination thereof.

24. A method for imaging or diagnosing a population of pathogenic cells, the method comprising the steps of contacting the population with one or more compositions of any one of the preceding clauses, and measuring a signal from the population.

25. Use of a therapeutically effective amount of one or more compositions of any one of the preceding clauses, one or more unit doses or unit dosage forms of any one of the preceding clauses, or a combination thereof in the manufacture of a medicament for treating cancer in a patient.

26. Use of one or more compositions of any one of the preceding clauses in a process for imaging or diagnosing a population of pathogenic cells, the method comprising the steps of contacting the population with the one or more compositions, and measuring a signal from the population.

27. The method or use of the preceding clause wherein the signal is a fluorescence signal.

28. The method or use of any one of the preceding clauses wherein the measuring step includes determining the red shift of the fluorescent signal.

29. The method or use of any one of the preceding clauses wherein the compound makes an energetically positive interaction with one or more of the residues selected from the group consisting of L150, L155, L168, and R53 on uPAR.

30. The method or use of any one of the preceding clauses wherein the compound makes an energetically positive interaction with L168 uPAR.

31. The method or use of any one of the preceding clauses wherein the compound makes an energetically positive interaction with R53 uPAR.

32. The method or use of any one of the preceding clauses wherein the total of all interactions with uPAR is less than or equal to about −10 kcal/mol.

33. The method or use of any one of the preceding clauses wherein the total of all interactions with uPAR is less than or equal to about −12 kcal/mol.

34. The method or use of any one of the preceding clauses wherein the total of all interactions with uPAR is less than or equal to about −14 kcal/mol.

35. The method or use of any one of the preceding clauses wherein the interaction with L150 is less then about −2 kcal/mol.

36. The method or use of any one of the preceding clauses wherein the interaction with L150 is less then about −2.25 kcal/mol.

37. The method or use of any one of the preceding clauses wherein the interaction with L150 is less then about −2.5 kcal/mol.

38. The method or use of any one of the preceding clauses wherein the interaction with L168 is less then about −1 kcal/mol.

39. The method or use of any one of the preceding clauses wherein the compound makes an energetically positive interaction with R53 on uPAR.

40. The method or use of any one of the preceding clauses wherein the interaction with R53 is greater than that of GFD.

41. The method or use of any one of the preceding clauses wherein the interaction with R53 is less then about −2.5 kcal/mol.

42. The method or use of any one of the preceding clauses wherein the interaction with R53 is less then about −3 kcal/mol.

43. The method or use of any one of the preceding clauses wherein the interaction with R53 is less then about −4 kcal/mol.

44. The method or use of any one of the preceding clauses wherein the interaction with R53 is less then about −5 kcal/mol.

In each of the foregoing clauses, and foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

It is also to be understood that in each of the foregoing, any corresponding pharmaceutically acceptable salt is also included in the illustrative embodiments described herein. Illustrative derivatives include, but are not limited to, both those compounds that may be synthetically prepared from the compounds described herein, as well as those compounds that may be prepared in a similar way as those described herein, but differing in the selection of starting materials. For example, described herein are compounds of the formulae above that include various functional groups on aromatic rings, such as X, $X^1$, Y, $Y^1$, $R^A$, and $R^{A1}$. It is to be understood that derivatives of those compounds also include the compounds having for example different functional groups on those aromatic rings than those explicitly set forth in the definition of the formulae. In addition, it is to be understood that derivatives of those compounds also include the compounds having those same or different functional groups at different positions on the aromatic ring. Similarly, derivatives include parallel variations of other functional groups on the compounds described herein, such as Y, and the like. It is to be understood that such derivatives may include prodrugs of the compounds described herein, compounds described herein that include one or more protection or protecting groups, including compounds that are used in the preparation of other compounds described herein.

Illustrative analogs include, but are not limited to, those compounds that share functional and in some cases structural similarity to those compounds described herein.

In addition, as used herein the term "analogs and derivatives thereof" also refers to prodrug derivatives of the compounds described herein, and including prodrugs of the various analogs and derivatives thereof. In addition, as used herein, the terms "compound" or "analog" or "derivative" refers to both the amorphous as well as any and all morphological forms of each of the compounds described herein. In addition, as used herein, the terms "compound" or "analog" or "derivative" refers to any and all hydrates, or other solvates, of the compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^x$, where x is an integer from 0-6 and $Z^x$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, amino alkyl, $C_1$-$C_6$ alkylaminoalkyl, ($C_1$-$C_6$ alkyl)($C_1$-$C_6$ alkyl)aminoalkyl, alkylcarbonylamino alkyl, N—($C_1$-$C_6$ alkyl)alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylamino ethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl and optionally substituted heteroaryl ($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

The compounds described herein may be prepared as described, and/or using conventional synthetic processes. Illustratively, the compounds described herein may be prepared as illustrated for the sodium salt of IPR-803, in the following scheme.

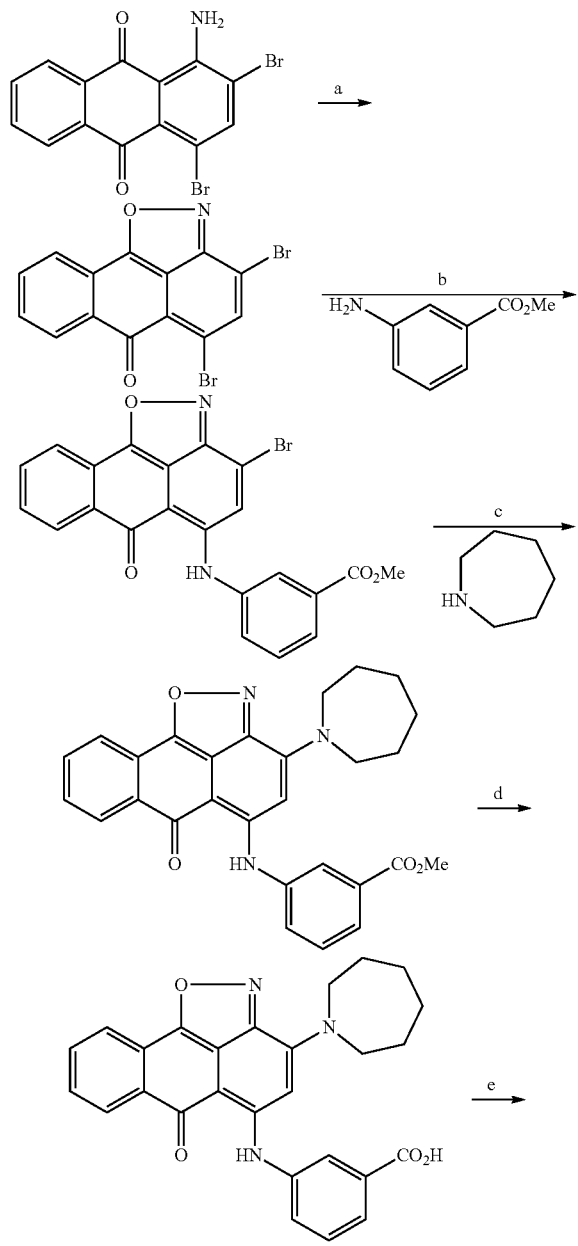

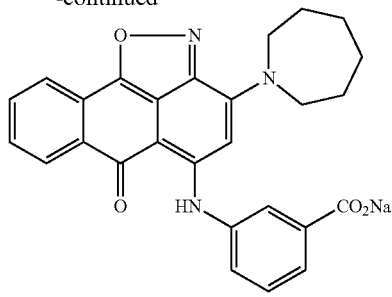

a) NOHSO$_4$/H2SO$_4$, NaN$_3$, toluene, reflux; b) AlCl$_3$, nitrobenzene, r.t.; c) acetonitrile, 80° C.; d) aq. NaOH/MeOH 80° C.; e) NaH, THF, r.t.

Briefly, 3,5-dibromo-6H-anthra[1,9-cd]isoxazol-6-one (1) was prepared by the diazotation of 1-amino-2,4-dibromoanthraquinone by adding sodium nitrite to a solution of the amine in concentrated sulfuric acid to give the 1-anthraquinonediazonium hydrogen sulfate which was subsequently converted to the 1-azidoanthraquinone by reacting with an aqueous solution of sodium azide. The azidoanthraquinone was azeotropically refluxed in toluene to provide, by evolution of nitrogen, the required isoxazole ring (1). Arylamination of 1 at the 5-position was accomplished with anhydrous AlCl$_3$ in nitrobenzene at ambient temperature to give a moderate yield of the 6-arylamino substituted compound (2). A second amination was carried out at the 3-position using refluxing acetonitrile to give a moderate yield of (3). Next, hydrolysis of the benzoate ester (3) to the carboxylic acid (4) occurred under conditions of heating an aqueous solution of sodium hydroxide and methanol. The sodium carboxylate salt (5) was synthesized quantitatively by reacting (4) with sodium hydride in THF at room temperature.

It is to be understood that the foregoing scheme may be adapted for the preparation of other compounds described herein by the appropriate selection of starting materials.

The following examples further illustrate specific embodiments of the invention; however, the following illustrative examples should not be interpreted in any way to limit the invention.

EXAMPLES

Example

Virtual Screening and Free Energy Calculations. Nearly 5 million lead-like compounds were virtually screened against uPAR crystal structures (PDB ID: 1YWH and 2FD6). Post-docking analysis was performed to assess and score the docked uPAR-compound complexes. The 2,000 most favorable compounds predicted by each scoring function were combined to give ~10,000 compounds pertaining to each crystal structure, which were further targeted to 50 conformers collected from explicit solvent MD simulations. Free energy calculations were carried out as described previously (43. Li et al. (2007) A computational investigation of allostery in the catabolite activator protein. Journal of the American Chemical Society 129(50):15668-15676).

Two uPAR 3D crystal structures were obtained from RCSB PDB (PDB ID: 1YWH and 2FD6). Structures were imported into SYBYL 8.0, a molecular modeling suite from Tripos Inc., for pre-docking preparation. All binding partners, ions and water molecules were removed. Missing gaps were modeled using BIOPOLYMER module in SYBYL. Hydrogen atoms were added and protonation states were optimized with Reduce (vers 3.03) program (102. Word et al. (1999) Asparagine and glutamine: using hydrogen atom contacts in the choice of side-chain amide orientation. *Journal of molecular biology* 285(4):1735-1747). Structures were then loaded into AutoDockTools (103. Sanner (1999) Python: A programming language for software integration and development. *Journal of Molecular Graphics & Modelling* 17(1):57-61). Gasteiger charges were assigned. Non-polar hydrogen atoms were merged. A binding box with side length of 15 Å was defined to encompass the uPA binding site. Autodock4 (104. Morris et al. (1998) Automated docking using a Lamarckian genetic algorithm and an empirical binding free energy function *Journal of Computational Chemistry* 19(14):1639-1662) was employed to dock compounds onto crystal structures. Default docking parameters were used. In total, nearly 5 million lead-like compounds from six vendors (ChemDiv, ChemBridge, Enamine, Aurora, IBScreen) listed on ZINC8 website (105. Irwin & Shoichet (2005) ZINC-A free database of commercially available compounds for virtual screening. *J Chem Inf Model* 45(1):177-182) were screened. The virtual screening was carried out on the IU Big Red supercomputer cluster. Post-docking analysis was performed to assess and score the docked uPAR/compound complexes. A set of scoring functions, including ChemScore, GoldScore, PMF, Autodock4, X-score and DFIRE and consensus scoring function, were employed to score the docked complexes. Compounds were ranked based on the score they received. The 2,000 most favorable compounds predicted by each scoring function were combined to give ~10,000 compounds pertaining to each crystal structure, which were further screened using multiple conformer strategy.

Explicit solvent MD simulations were performed to sample uPAR conformations in solution. To perform MD simulations, crystal structures prepared with SYBYL were solvated with TIP3P (106. Jorgensen et al. (1983) Comparison of simple potential functions for simulating liquid water. *The Journal of Chemical Physics* 79(2):10) water molecules and were further neutralized with $Na^+$ or $Cl^-$ counter ions using Leap program from the AMBER9 package (107. Case et al. (2004) AMBER 8 (University of California, San Francisco)). Water molecules from crystal structures were retained in this process. A deliberate annealing process described elsewhere (108. Li et al. (2007) A computational investigation of allostery in the catabolite activator protein *Journal of the American Chemical Society* 129(50):15668-15676) was employed to equilibrate the solvated structures before production runs were carried out. The pmemd in AMBER was employed for production runs. MD snapshots were saved every 2 ps, which results in 5,000 structures per trajectory. By assigning different initial velocities, five independent simulation trajectories on each of the crystal structures in length of 10 ns were collected. Structures from MD were clustered focusing on the heavy atoms on the uPA binding site using ptraj program in AMBER. A total of 50 conformers (25 each on 1YWH and 2FD6) with distinct pocket structures were selected. Top compounds (~10,000) emerging from screening against two crystal structures were then docked onto corresponding multiple conformers using Autodock4. The docked complexes were scored with ChemScore and GoldScore. Top 500 compounds showing best binding affinity predicted by ChemScore and GoldScore respectively among multiple conformers were selected, which were further docked onto conformers using Glide (Glide, version 5.5, Schrödinger, LLC, New York, N.Y., 2009). The flexible ligand docking protocol of Glide SP with default parameters were used. Compounds with the best Glide scores among all the docked uPAR/ligand complexes were selected and purchased for in vitro testing.

Example

Binding Energy Calculations. The binding energy of compounds and peptide to uPAR protein was calculated with MM-PBSA/GBSA approach (109. Chong et al. (1999) Molecular dynamics and free-energy calculations applied to affinity maturation in antibody 48G7. *Proc Natl Acad Sci USA* 96(25):14330-14335) following multi-trajectory MD simulation on the complexes, for which the setup process is akin to simulations on uPAR apo form. The compound conformation on uPAR was provided from docking results while the peptide bound conformation was extracted from PDB structure (PDB ID: 3BT1). AM1-BCC (110. Jakalian et al. (2002) Fast, efficient generation of high-quality atomic charges. AM1-BCC model: II. Parameterization and validation. *J Comput Chem* 23(16):1623-1641) charges were assigned to compounds by the antechamber program in the Amber9 package. For each complex, 6 independent simulations in length of 8 ns were carried out after annealing runs. The initial segment (2-3 ns) on each trajectory was excluded from binding energy calculations as the system is less equilibrated. In total, 600 snapshots were extracted evenly from the production trajectories and subject to MM-PBSA/GBSA energy analysis. The MM-PBSA perl scripts in Amber9 were employed to compute binding energy components and to decompose the binding energy on a per residue basis (111. Gohlke et al. (2003) Insights into protein-protein binding by binding free energy calculation and free energy decomposition for the Ras-Raf and Ras-RalGDS complexes. *J Mol Biol* 330(4):891-913). The latter is believed to provide a useful insight on the relative importance of residues on the pocket to the binding of ligand to uPAR.

Example

Computational Search of Chemical Databases. A total of 80,000 structures from MD simulations were distilled into a representative set of 50 conformations. Root-mean-square (r.m.s.) deviation calculations reveals significant differences of these conformers with the uPAR crystal structure (PDB code: 1YWH) (overall r.m.s. derivation using backbone residues ranged from 1.5 to 7 Å). Docking efforts targeting these conformers were concentrated at the growth factor-like (GFD) binding site of uPA, which is believed to contain the majority of hot-spots and to be responsible for more than 90% of the uPA affinity (19). A multi-tier virtual screening approach was implemented that consisted of first docking 5 million compounds to uPAR crystal structures and selecting the top 10,000 compounds that were in turn docked to the 50 conformations that emerged from MD. Compounds were ranked independently for each conformer, and top candidates for each conformer were combined and ranked again, culminating in the selection of 50 compounds.

Example

Free Energy Calculations and their Insight into Binding Mechanism. Without being bound by theory, it was hypothesized that part of the reason that IPR-456 inhibited the full protein interactions may be attributed to specific interactions of the compounds with uPAR. To test this hypothesis, intensive explicit-solvent MD simulations complemented by free energy calculations were used following the widely used MM-GBSA approach reported in the literature (28. Liang et al. (2009) Exploring the molecular design of protein interaction sites with molecular dynamics simulations and free energy calculations. Biochemistry 48(2):399-414; 29. Li L, Liang et al. (2009) Incorporating receptor flexibility in the molecular design of protein interfaces. Protein Eng Des Sel 22(9):575-586; 30. Li et al. (2007) A computational investigation of allostery in the catabolite activator protein. Journal of the American Chemical Society 129(50):15668-15676). The calculations consisted of computing components of the free energy of binding that consist of: (i) a non-polar component ($\Delta E_{NP}=\Delta E_{VWD}+\Delta E_{SA}$), which comprises the sum of the van der Waals potential energy and non-polar solvation energy; (ii) a polar component ($\Delta E_{ELE}=\Delta E_{COUL}+\Delta E_{GB}$), which consists of the Coulomb electrostatic energy and the Generalized-Born solvation energy and; (iii) entropy (T$\Delta$-$S_{NM}$), which is a reflection of the order created upon binding of compound to its receptor. The sum of these components corresponds to the GBSA binding free energy $\Delta G_{GBSA}$, are shown in the following table.

| | Compound binding energy to uPAR calculated by MM-PBSA/GBSA approach (in unit of kcal · mol$^{-1}$) | | | | |
|---|---|---|---|---|---|
| | $\Delta E_{ELE}$ | $\Delta E_{NP}$ | $\Delta E_{GBTOT}$ | T$\Delta S_{NM}$ | $\Delta G_{GBSA}$ |
| IPR-456 | 22.3 ± 0.1 | −57.5 ± 0.1 | −36.0 ± 0.2 | −24.9 + 0.5 | −11.1 ± 0.5 |
| GFD | 41.4 ± 0.4 | −116.3 ± 0.4 | −77.9 ± 0.5 | −48.9 ± 0.5 | −29.0 ± 0.7 |

$\Delta E_{VDW}$, van der Waals potential energy; $\Delta E_{PBELE}$, electrostatic contributions to the binding energy, of which the polar solvent contributions were calculated with Poisson-Boltzmann equation; $\Delta E_{GBELE}$, electrostatic contributions to the binding energy, of which the polar solvent contributions were calculated with Generalized Born equation; $\Delta E_{SA}$, nonpolar solvent contribution to solvation free energy; $\Delta E_{PBTOT}$, the sum of $\Delta E_{VDW}$, $\Delta E_{PBELE}$ and $\Delta E_{SA}$; $\Delta E_{GBTOT}$, the sum of $\Delta E_{VDW}$, $\Delta E_{GBELE}$ and $\Delta E_{SA}$; T$\Delta S_{NM}$, entropy calculated with normal mode analysis; $\Delta G_{PB}$, the calculated free energy of binding using PB model; $\Delta G_{GB}$, the calculated free energy of binding using GB model.

In general it has been reported that the absolute values of $\Delta G_{GBSA}$ do not exactly correspond to experimental binding free energy, but the trends may reflect those observed experimentally (31. Neugebauer et al. (2008) Structure-activity studies on splitomicin derivatives as sirtuin inhibitors and computational prediction of binding mode. Journal of medicinal chemistry 51(5):1203-1213; 32. Guimaraes & Cardozo (2008) MM-GB/SA Rescoring of Docking Poses in Structure-Based Lead Optimization. J Chem Inf Model 48(5):958-970; 33. Gohlke & Case (2004) Converging free energy estimates: MM-PB(GB)SA studies on the protein-protein complex Ras-Raf. Journal of Computational Chemistry 25(2):238-250; 34. Yang et al. (2009) Importance of ligand reorganization free energy in protein-ligand binding-affinity prediction. Journal of the American Chemical Society 131(38):13709-13721). In the case herein, it may be interesting that $\Delta G_{GBSA}$ appears to correctly identify GFD ($K_i$=0.22 µM) to be more potent than IPR-456 ($K_i$=4.0 µM). The calculations, which appear to be in agreement with experiment, may be taken to show a $\Delta G_{GBSA}$ value for IPR-456 of −11.0 kcal·mol$^{-1}$.

To gain insight into the contributions of each residue to the binding of compounds to uPAR, residue-based free energy calculations ($\Delta E_{RES}$) were performed. The interaction energy between the residue ($\Delta E_{GBTOT}$) is shown in parentheses in kcal·mol$^{-1}$. Only residues with $\Delta E_{GBTOT} \leq -1.0$ are listed for IPR-456 compared to GFD in the following table.

| | | | | $\Delta$Eres (kcal/mol) | | | |
|---|---|---|---|---|---|---|---|
| IPR-456 | R53 | L150 | V125 | L55 | L144 | L168 | A255 |
| | (−5.3)[B] | (−2.7)[A] | (−1.8)[B] | (−1.5)[A] | (−1.2)[C] | (−1.1)[A] | (−1.0)[C] |
| GFD | R53 | T127 | H166 | L150 | D254 | D140 | L55 |
| | (−2.4)[B] | (−2.3)[A] | (−1.8)[C] | (−1.7)[A] | (−1.7)[C] | (−1.5)[A] | (−1.5)[A] |

[A]residues having a penalty greater than 0.5 kcal · mol$^{-1}$ and less than 1 kcal · mol$^{-1}$ for uPA binding to uPAR from an alanine scanning surface plasmon resonance (SPR) study (19, 35. Gardsvoll et al. (2004) Characterization of low-glycosylated forms of soluble human urokinase receptor expressed in *Drosophila* Schneider 2 cells after deletion of glycosylation-sites. Protein expression and purification 34(2): 284-295);
[B]residues having more than 1 kcal·mol$^{-1}$ loss of affinity for uPA;
[C]residues that did not show any effect on binding of uPA from the SPR study.

IPR-456 appears to have come in contact with a total of 7 residues. In addition, IPR-456 seems to engage several hot-spot residues (L150, L55 and L168). In addition, IPR-456's interaction with these hot-spot residues appears to be strong. Another observation is that the sum of the individual interaction energies across all the amino acids that come in contact with the compound appears to be great for IPR-456 (−14.6 kcal·mol$^{-1}$). Finally, it appears that IPR-456 forms the strongest interaction with R53 (−5.3 kcal·mol$^{-1}$), which is also found to be the residue that seems to most strongly interact with GFD (−2.4 kcal·mol$^{-1}$). Alanine scanning experiments were reported to show that R53 contributed nearly 0.9 kcal·mol$^{-1}$ to uPA binding (35). Without being bound by theory, it is believed herein that R53 is a particularly important interaction for binding and efficacy. Without being bound by theory, analysis of the trajectories of the uPAR•GFD complex may be taken to indicate that the carbonyl oxygen of Y24 on GFD forms a hydrogen bond interaction with one of the nitrogen atoms on the guanidinium ion of R53. Like GFD, the structure of IPR-456 bound to uPAR crystal structure may reveal that the compound forms a hydrogen bond with R53 through a carbonyl oxygen on its antraquinone ring as well as its carboxylate moiety with a 50% occupancy for each computed over all the snapshots collected in the MD simulations.

Reagents

Mouse anti-human uPAR antibody 3937 and rabbit anti-human uPA antibody 389 were purchased from America Diagnostica Inc (Stanford, Conn.). Biotinylated anti-human uPAR antibody was purchased from R&D Systems, Inc (Minneapolis, Minn.). uPAR siRNA and control siRNA were purchased from Santa Cruz Biotechnology Inc (Santa Cruz, Calif.).

Example

Protein Purification. uPAR comprising amino acids 1-277 was expressed in *Drosophila* S2 cells and purified by a peptide column as described in the literature (101. Gardsvoll et al. (2007) A new tagging system for production of recombinant proteins in *Drosophila* S2 cells using the third domain of the urokinase receptor. Protein expression and purification 52(2): 384-394). The purified protein was analyzed with SDS-PAGE gel and found to be greater than 95% purity. The protein was determined to be functional based on a fluorescence polarization (FP) assay developed as discussed below, as well as binding to immobilized uPA using surface plasmon resonance (SPR). The soluble fraction of uPA (scuPA) and uPA$_{ATF}$ (amino terminal fraction of uPA) were purified by an anion exchange column (SP Sepharose). This was followed by a second step of purification with a reverse phase-HPLC purification using a $C_8$ column where the protein is eluted with an increasing gradient of acetonitrile over 1 hour.

Example

Cell Culture. H1299 cells were maintained in RPMI-1640 medium (Cellgro, Manassas, Va.). MDA-MB-231 cells were cultured in Dulbecco's Modified Eagle Medium (DMEM, Cellgro, Manassas, Va.). Each medium was supplemented with 10% FBS, 1% penicillin/streptomycin in a 5% $CO_2$ atmosphere at 37° C.

Example siRNA Knockdown and Western Blot Analysis. MDA-MB-231 cells were transfected with mock, control siRNA or uPAR siRNA by lipofectamine 2000 (Invitrogen, Carlsbad, Calif.) according to the protocol. H1299 and MDA-MB-231 were incubated for 48 hrs. Cells were then collected, and total cell lysates were prepared in standard RIPA extraction buffer containing aprotinin and phenyl-methyl-sulfonyl-fluoride. Twenty micrograms of protein from these samples were separated by 12% SDS-PAGE and transferred to nitrocellulose membranes (Amersham, Arlington Heights, Ill.). The membranes were immunoprobed with antibodies against biotin-uPAR at 4° C. overnight. Next, membranes were treated with the appropriate HRP-conjugated secondary antibody and then developed according to enhanced chemiluminescence protocol (Thermo Scientific, Rockford, Ill.). Membranes were stripped and probed with monoclonal antibody for actin as loading control.

Example

Microtiter-Based ELISA. The competition-binding assays were performed by incubating the proteins with inhibitors prior to binding to the immobilized proteins. Medium to high-binding microplates were coated and incubated for 1 hour at 4° C. with 100 µL of 2 µg/mL of uPA$_{ATF}$ in 1×PBS for immobilization. A 1:1 mixture of Superblock® buffer in PBS (Thermoscientific) with 0.04 M $NaH_2PO_4$ and 0.3 M NaCl buffer were used for blocking Following the incubation and washing steps, uPA1310 biotinylated antibody (R&D Systems, MN) in 1% BSA 1×PBS buffer (100 µL/well) was added to the wells and incubated for 1-2 hours to allow for the detection of bound uPAR. In the presence of streptavidin-peroxidase and hydrogen peroxide signal was detected on an EnVision® Multilabel Plate Readers (PerkinElmer).

Example

Immunofluorescence Imaging. An immunofluorescence approach was employed to establish the specificity of the compounds. This consisted of using a fluorescently labeled secondary antibody to probe for the presence of an anti-uPA antibody bound to uPA at the cell surface of MDA-MB-231 and H1299 cancer cells. H1299 and MDA-MB-231 cells were grown on laminin-coated glass coverslips, exposed to 100 µM of IPR-456 for 30 min at 37° C., washed with PBS, fixed with 4% paraformaldehyde for 20 min, and permeabilized with 1% Triton X-100 for 10 min. Non-specific bindings were blocked with 5% normal goat serum, 5% BSA, 0.01% Triton X-100 in PBS at RT for 1 h, the cells were then incubated overnight at 4° C. with rabbit polyclonal anti-human uPA or mouse monoclonal anti-human uPAR antibodies (both at a dilution of 1:100 in 1% BSA/PBS). After another washing step with PBS three times, the cells were incubated with anti-rabbit IgG conjugated with Alexa 594 Texas Red (Invitrogen Corporation, Carlsbad, Calif.) or goat anti-mouse IgG conjugated with Alexa Fluor 488 (Invitrogen Corporation, Carlsbad, Calif.), both at a dilution of 1:1000 in 1% BSA/PBS at RT for 1 h in the dark. Images were acquired using a Nikon swept-filed confocal microscope.

Example

Fluorescence Polarization Assay. A fluorescence polarization assay was developed that consists of fluorescent GFD peptide (FAM-CLNGGTCVSNKYFSNIHWCN (SEQ ID NO: 1); Antagene Inc, CA). uPAR was titrated against the fluorescent GFD-FAM peptide and data was fit to a sigmoidal dose-dependent curve as the FP value increases to determine the $K_d$ of binding using Sigmaplot (Systat Software Inc., CA) Inhibitor screens were carried out in triplicates using 500 nM uPAR, 50 nM GFD-FAM, and inhibitor concentrations ranging from 0.78 µM to 100 µM in 50 µL volumes in black BD Falcon 384-well microplate. The compounds were serially diluted in DMSO then diluted in to 0.01% Triton X-100 in 1×PBS buffer ensuring a final concentration of 2% DMSO (a concentration that did not affect peptide binding to uPAR). Polarized fluorescence intensities were measured immediately following addition of inhibitors to the protein-peptide mix at room temperature on an EnVision® Multilabel Plate Readers (PerkinElmer) with excitation and emission wavelengths of 485 and 530 nm, respectively.

For inhibitors that had fluorescence at higher wavelength, an excitation of 530 nm and emission of 600 nm were used to detect direct binding. Fluorescence polarization in the presence and absence of protein and were measured using identical conditions as described above. Both IPR-456 and IPR-803 showed a dose response with increasing mP as a function of increasing uPAR concentration.

Example

Fluorescence Polarization Screening to Identify Hit Compounds. To identify compounds that bind to uPAR at the GFD binding site, a fluorescent polarization assay is conceived with a probe that consists of labeling GFD with fluorescein at its N-terminus (GFD-FAM). GFD-FAM is shown to bind strongly to uPAR with a dissociation equilibrium constant ($K_D$) of 0.120 µM. Using this assay, all compounds that emerge from the computational screening are tested initially at a single concentration of 50 µM. The compounds showing the highest reduction in polarization are subjected to activity confirmation. To confirm activity, a concentration dependent study selects those compounds that displace GFD-FAM, using unlabeled GFD peptide as a control ($K_i$=0.22 µM). Illustratively, compound IPR-456 exhibited a $K_i$ value of 4 µM.

Example

IPR-456 Inhibition of uPAR•uPA Binding. To establish whether compounds that displace the peptide also abrogate the full uPAR•uPA interaction, a microtiter-based ELISA was developed using uPAR and the amino-terminal fragment (uPA$_{ATF}$), which includes the entire binding surface of full-length uPA (20). Compounds described herein, such as IPR-456, are tested at multiple concentrations for assessing inhibition of uPAR binding to uPA using this uPA$_{ATF}$ ELISA. IPR-456 showed complete concentration dependent inhibition of uPA$_{ATF}$ binding to uPAR with an estimated IC$_{50}$ of 10 µM.

Example

Specific Binding of IPR-456 to the GFD Site on uPAR. To address the question of whether IPR-456 binds at the intended targeted site on uPAR, the inherent red-shifted fluorescence of IPR-456 at longer wavelengths in the spectrum was exploited to measure fluorescence polarization changes as a result of direct binding to uPAR. In addition, fluorescence polarization (mP) for IPR456 was measured at 600 nm with increasing concentration of uPAR. The mP was evaluated in the a presence and absence of competing 10 µM GFD. Increasing concentration of uPAR appears to have led to a corresponding increase in the measured fluorescence polarization, which may be taken as confirming direct binding between IPR-456 and with a K$_d$ of 0.312 µM. The affinity of the compound is similar to that of GFD-FAM and akin to the K$_i$ that was measured for IPR-456 inhibition of GFD binding to uPAR. To confirm whether IPR-456 indeed binds at the GFD site, the aforementioned experiment was repeated by increasing the concentration of uPAR but in the presence 10 µM GFD. When evaluated with competing GFD, that no change in the polarization was detected, which may be taken as suggesting that GFD blocked IPR-456 binding to uPAR and confirming that the compound was competing with GFD for the same site on the receptor. Without being bound by theory, it is hypothesized that this observation strongly argues against any potential inhibition due to non-specific effects such as aggregation (27. Feng & Shoichet (2006) A detergent-based assay for the detection of promiscuous inhibitors. Nat Protoc 1(2):550-553). Other evidence that may argue against non-stoichiometric binding due to aggregation include (i) the high level of binding of IPR-456 to uPAR, even at sub-micromolar concentrations, (ii) strong binding as well as inhibition even in the presence of detergent (0.01% Triton X-100), and (iii) the lack of steepness in the binding and inhibition curves.

Example

Integrin Signaling. Compounds described herein do not show appreciable binding or signaling of integrins, and in particular phospho p44/42 MAPK, p44/42 MAPK, pSrc Y416, Src, pFAK Y397, and FAK, as determined by gel electrophoresis at 1, 10, 25, or 50 µM.

Example

IPR-456 Abrogation of uPAR•uPA Binding in Tumor Cells. Interference of compound IPR-456 with the surface distribution of uPA in lung (H1299) and breast (MDAMB231) cancer cells. Immunofluorescence techniques were used to directly visualize the effect of IPR-456 on the uPAR•uPA interaction at the cell surface. Endogenous uPAR and uPA in the non-small cell lung cancer (NSCLC) cell line H1299 and in a breast cancer cell line MDA-MB-231 were immunostained with selective antibodies and visualized by staining with fluorescently-conjugated secondary antibodies. Cells are stained with (a) a monoclonal antibody against uPAR or (b) a polyclonal antibody against uPA.

Figure 1B:
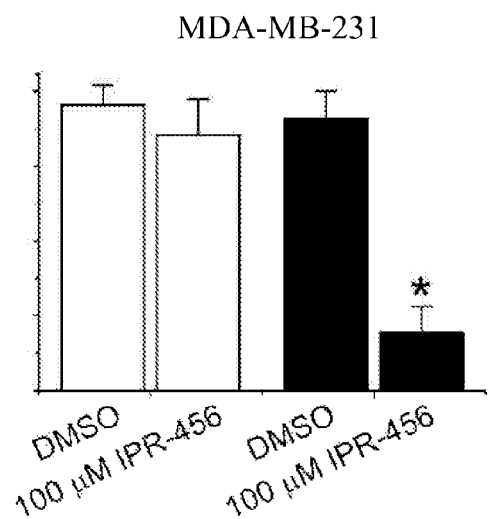

To get a quantitative estimate of the effect of IPR-456 on the uPAR and uPA levels the surface staining intensity for both proteins was quantified. In cells with clear surface staining, the surface of each cell was outlined using uPAR staining and then the pixel immunodensity for uPAR and uPA were determined using Nikon elements software in the outlined regions. Only cells where the cell membrane was clearly discernible were included in the analysis. Results are shown in FIG. 1(a) and FIG. 1(b). Each value represents the mean±S.E. from 26-30 cells taken from three different fields from two independent samples. *significant difference from the DMSO control (p<0.001, Student's t test). In the absence of any compound (0.1% DMSO; vehicle control) both uPAR and uPA were detected in large intracellular clusters as well as on surface membranes of MDA-MB-231 cells. In the presence of 100 µM IPR-456, added 30 minutes prior to immunostaining, there seems to have been a significant reduction of uPA staining at the cell surface in both cell types. In contrast, it appears that there was no change in the immunostaining pattern of uPAR when compared to DMSO control. Without being bound by theory, it is believed herein that these data arise from uPAR being tethered to the cell surface through a GPI anchor, while uPA is soluble. Also without being bound by theory, it is believed herein that these results support that IPR-456's action was not via a non-specific down-regulation of uPAR, but rather by preventing uPA from binding to uPAR, in line with biochemical assays that IPR-456 acts as a direct inhibitor of the protein interaction.

Example

Figure 2A:
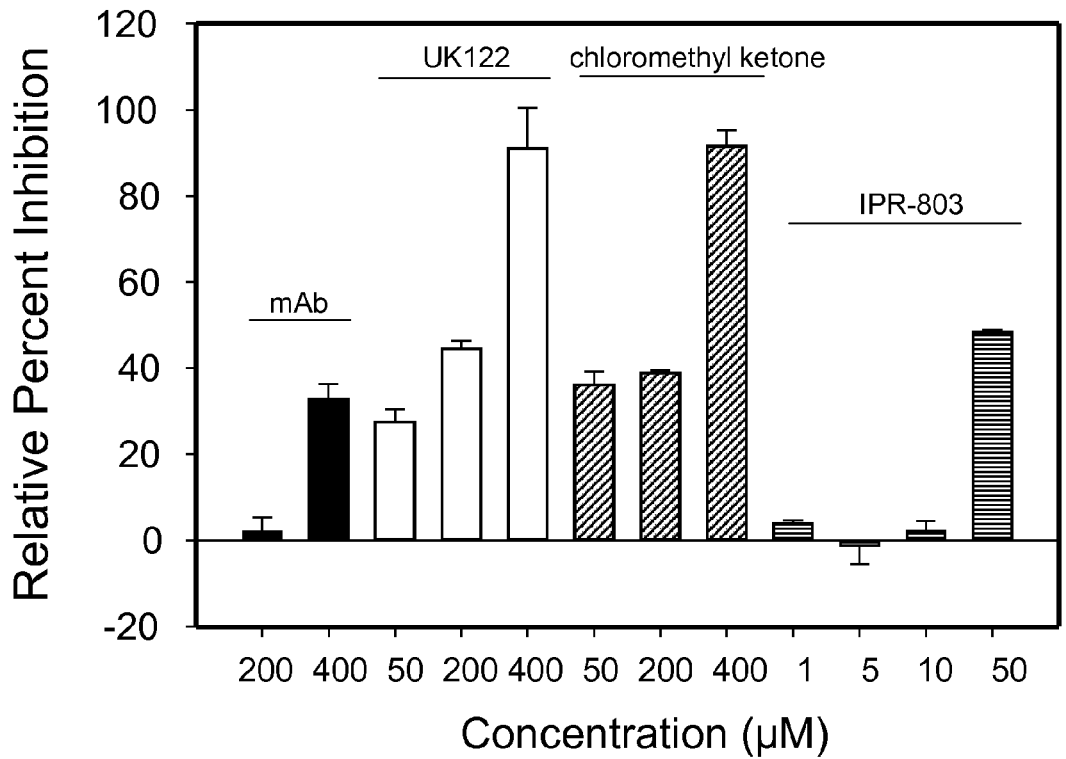
FIG. 2 shows relative percent inhibition as a dose response, (a) comparing IPR-803 to mAb, UK122, and chloromethyl ketone in A549 cells, and (b) comparing IPR-456 and IPR-803 to DMSO control in MDA-MB-231 cells.
Figure 2B:
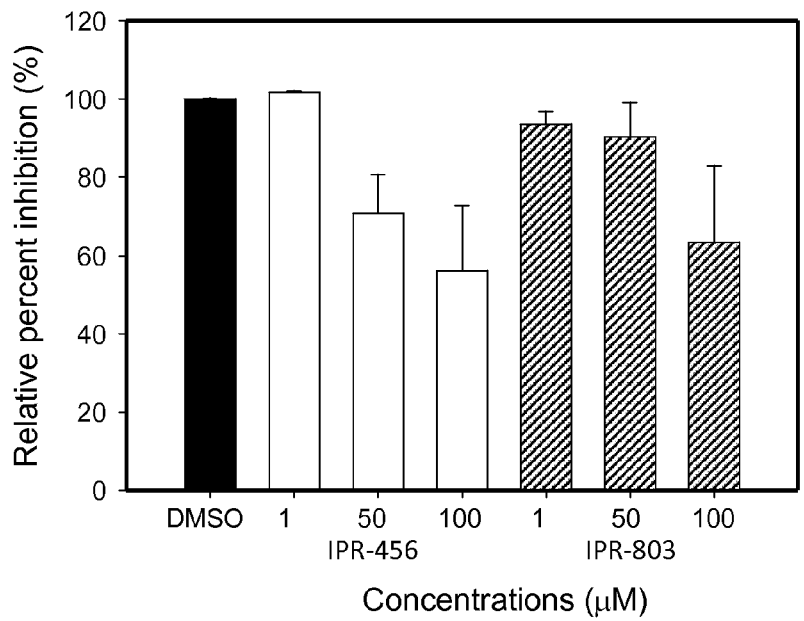

Fluorescence assays of cell surface-bound HMW-uPA activity in A549 cells. This Example is performed as described in Khanna et al. (2011) Targeting multiple conformations leads to small molecule inhibitors of the uPAR•uPA protein-protein interaction that block cancer cell invasion, ACS Chem Biol 6, 1232-1243, the disclosure of which is incorporated herein in its entirety. Briefly, A549 cells were pre-incubated for 30 min with a range of concentrations of Ab3937, UK122, chloromethyl ketone or IPR803. Cells were washed, fluorogenic uPA-specific substrate added and fluorescence measurements recorded. Initial rates of change in fluorescence after subtraction of background fluorescence (cells only) are presented as a percentage of control (no test compound added). Values represent means±SD (n=3) obtained from representative experiments, as shown in FIG. 2(a) and FIG. 2(b).

Example

Invasion Assay. Invasion assays are performed using the Biocoat Matrigel invasion chamber (BD Biosciences, Bedford, Mass.) according to the manufacturer's protocol. The undersurface of the inserts were coated with 30 ng/µl of fibronectin at 4° C. overnight. The filters were equilibrated with 0.5 ml serum-free medium for 2 h. After 4 h of serum starvation, cells were harvested and 5×10$^4$ cells/500 µl were plated onto the upper chamber of a Transwell filter in medium containing 0.1% FBS and the indicated compounds. 500 µl of 10% FBS medium containing the same amount of compounds or DMSO control were added to the lower chamber. After a 24 h incubation at 37° C. in 5% CO$_2$, the filters were fixed and the number of cells that had invaded was determined as described for the migration assay.

Example

Transwell Migration Assay. A 24 well transwell plates (Costar, Corning, N.Y.) were coated with fibronectin. After 4 h of serum starvation, medium containing the same amount of compounds or DMSO were added to the upper chamber and incubated at 37° C. for 8 h. The number of migrated cells was counted in 10 separate 200×fields and averaged over three independent experiments. Cytotoxicity of the compounds on the cells was measured at the same concentrations used in the migration assay during the same incubation time. MTT was added 2 h before measuring.

A 24 well transwell plates (Costar, Corning, N.Y.) were coated with 30 ng/µl of fibronectin at 4° C. overnight. 500 µl of 10% FBS RPMI-1640 medium containing compounds or 1% DMSO control was added to the lower chamber. After 4 h of serum starvation, $5 \times 10^4$ cells in 250 µl of 0.1% FBS medium containing the same amount of compounds or DMSO were added to the upper chamber and incubated at 37° C. for 8 h. Non-invaded cells on the top of the transwell were scrapped-off with a cotton swab, and the cells that had migrated through the filter were fixed in methanol for 30 min, stained with Hematoxylin Stain (Fisher, SH30-500D) for 1 h. The number of migrated cells was counted in 10 separate 200×fields and averaged over three independent experiments. Cytotoxicity of the compounds on the cells was measured at the same concentrations used in the migration assay during the same incubation time, MTT was added 2 h before measuring.

Example

Adhesion Assay. 96-well plates were coated with 15 ng/µl fibronectin (Sigma, St. Louis, Mo.) at 4° C. overnight, then blocked with 0.5% BSA in PBS for 1 h. After starving with serum-free medium for 3 h, H1299 or MDA-MB-231 ($2.5 \times 10^5$ cells/ml) were trypsinized and suspended in 100 µl of 0.1% FBS medium with various concentrations of uPAR compounds or DMSO control at 37° C. for 90 min. Medium was then carefully suctioned out from each well. Each well was washed three times with PBS. MTT-assay was used to determine the number of remaining cells (adherent cells).

Example

Wound Healing Assay. Confluent cell monolayers in 12-well plates were wounded by scraping with a micropipette tip. The cells were washed and then cultured in complete media containing the compounds. The degree of wound closure was assessed in three randomly chosen regions by measuring the distance between the wound edges just after wounding and after 16 h under Nikon Diaphot 300 microscope.

Example

Figure 3A:
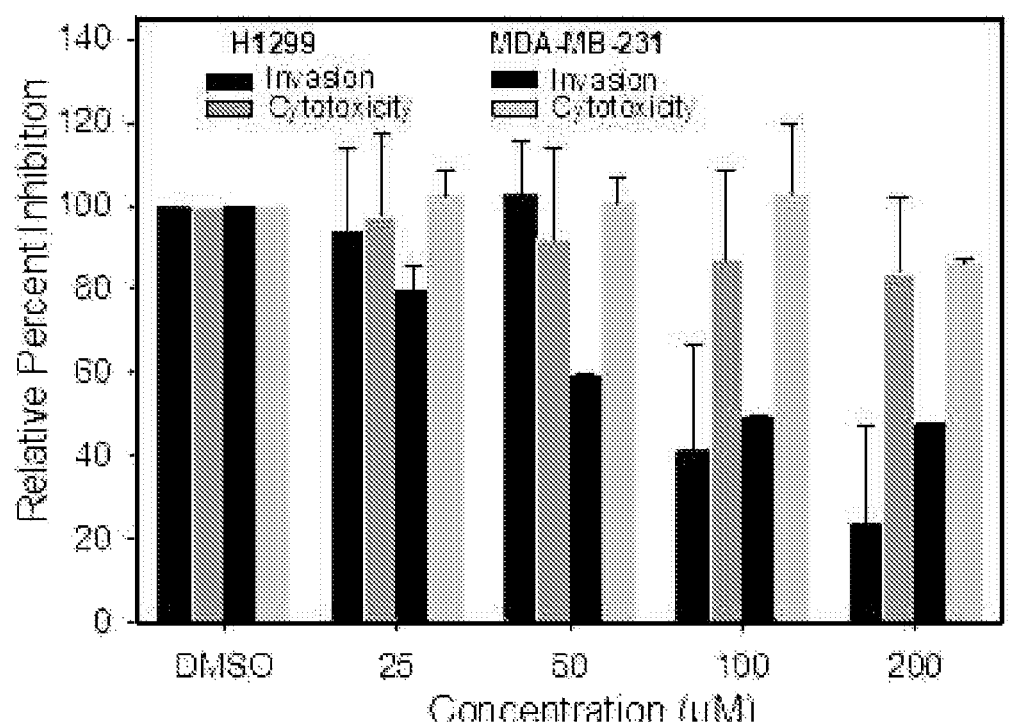
FIG. 3 shows relative percent inhibition as a dose response of IPR-456 in H1299 cells MDA-MB-231 cells, showing (a) invasion and cytotoxicity, and (b) Boyden Chamber, wound healing, and cytotoxicity.

IPR-456 Blocking of invasion, migration and adhesion in a cytotoxicity-independent process of lung (H1299) and breast (MDA-MB-231) cancer cells. Testing of the effects of IPR-465 on processes critical for metastasis in cell culture, starting with invasion, was undertaken. A Boyden chamber apparatus was used and results are shown in FIG. 3(a), where the bar groups correspond, from left to right, to H1299 invasion, H1299 cytotoxicity, MDA-MB-231 invasion, MDA-MB-231 cytotoxicity, and in FIG. 3(b), where the bar groups correspond, from left to right, to H1299 Boyden Chamber, H1299 wound healing, H1299 cytotoxicity, MDA-MB-231 Boyden Chamber, MDA-MB-231 wound healing, MDA-MB-231 cytotoxicity.

A dose-dependent reduction in the number of cells that are able to invade through the membrane is observed. The invasion of H1299 and MDA-MB-231 cells are shown in the absence or presence of IPR-456, as indicated in FIG. 3(a). Ten fields of unit area on each membrane were counted for cell numbers (magnification, 200×). These data represent the average ±SD of three independent experiments. *$P<0.05$, paired one-tailed t-test. The effect of the compound appears to be more pronounced in MDA-MB-231 cells compared with H1299. The level of toxicity of the compounds is measured at each concentration within the timescale of the invasion experiment to ensure that the observed effects are not due to cytotoxicity (FIG. 3(a)). The compound did not exhibit undue toxicity even at concentrations reaching 200 µM, which, without being bound by theory, may be taken as demonstrating that the observed effects on invasion are unlikely to be due to non-specific effects.

To assess that the effects on invasion observed for IPR-456 are due to uPAR, knockdown of the receptor was performed using small interfering RNA (siRNA). MDA-MB-231 cells were transfected with siRNAs for uPAR, control siRNA (control) or with transfection reagent only (mock). After 48 h, cells were lysed and analysed by immunoblotting. Invasion in the absence or presence of IPR-456 for H1299 and MDA-MB-231 with siRNA knockdown of uPAR. The invasive potential for these cells appears to be significantly impaired as a result of siRNA knockdown of uPAR by nearly 70% in both H1299 and MDA-MB-231 cells. IPR-456 appears to have no additional influence on invasion for H1299 and MDA-MB-231 with siRNA knockdown of uPAR. Without being bound by theory, it is believed herein that IPR-456 is blocking invasion specifically through its action in blocking the binding of uPA to uPAR.

Figure 3B:
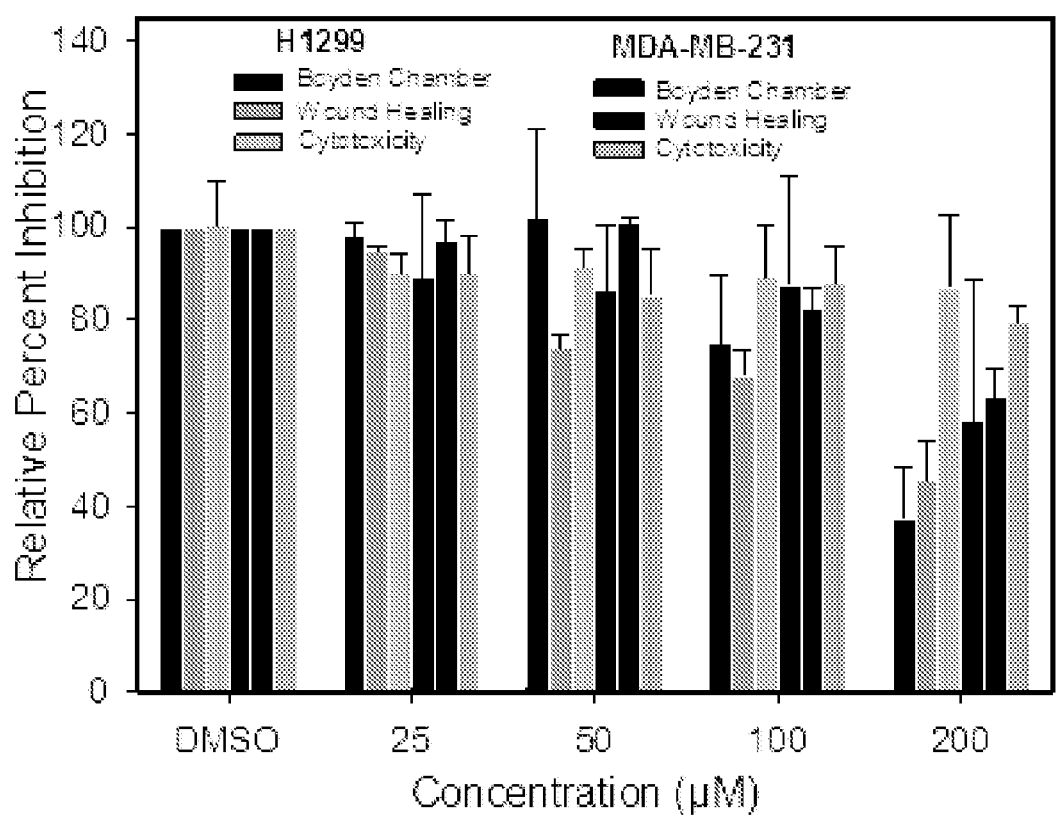

Example invasion of H1299 and MDA-MB-231 cells in the presence of increasing concentration of IPR-456. Without being bound by theory, it is believed that, to invade neighboring tissue, cells must acquire additional motility, although invasion and migration may proceed through different mechanisms. To test for the effect on migration of IPR-456, two different approaches were employed. The first uses the Boyden chamber apparatus to assess the effect of compound on migration primarily mediated by chemotaxis. Effect of compound IPR-456 on migration assessed by the wound healing (magnification 100×) and Boyden chamber assays (200×). As shown in FIG. 3(b), IPR-456 appears to have blocked migration in a dose-dependent manner but higher concentrations were needed to reach 50% inhibition compared with invasion. The other approach to test for effects on migration was the wound healing assay, which probes migration mediated by a concentration gradient established by the wound. It is also not as sensitive to potential cytotoxic effects. As in the Boyden chamber assay, the compound appears to have inhibited migration, with an $IC_{50} \sim 150$ µM. Cells were harvested to test for cytotoxicity, but none was observed for the compound.

To probe the role of IPR-456 in H1299 and MDA-MB-231 tumor cell adhesion, a solid phase assay was used where fibronectin or vitronectin are coated on a microtiter plate followed by addition of cells. The adhesion of H1299 and MDAMB231 cells to ECM components fibronectin (FN) or vitronectin (VN) in the absence or presence of IPR-456 was evaluated. The numbers of attached cells were quantified by MTT assay. Adherent cells are also quantified with fluorescence. Compound IPR-456 seems to show no effect on cell adhesion for both H1299 and MDA-MB-231 cancer cell lines. The lack of inhibition was found both on fibronectin- and vitronectin-coated wells.

Highly invasive tumor cells such as lung H1299 and breast MDA-MB-231 tumor cells have been reported to overexpress uPAR. Immuno fluorescence imaging in H1299 and MDA-MB-231 cells appeared to show that IPR-456 impairs binding of uPA to uPAR at the cell membrane. The lack of cytotoxicity of IPR-456 may be a reflection of the specificity of this compound and may also be consistent with reported studies in which it is believed that uPAR impairs cell growth, but it is not a lethal target (37. Hildenbrand et al. (2008) The urokinase-system-role of cell proliferation and apoptosis. Histology and Histopathology 23(2):227-236). It is also reported that uPAR-deficient mice do not exhibit evidence of impairment in development or fertility (38. Bugge et al. (1995) The receptor for urokinase-type plasminogen activator is not essential for mouse development or fertility. The Journal of biological chemistry 270(28):16886-16894). IPR-456 appeared to impair H1299 and MDA-MB-231 invasion with $IC_{50}$ near 50 µM (FIG. 3(a)). But milder effects on migration were observed with $IC_{50}$~150 µM. It is worth noting the differences in the $IC_{50}$ values for IPR-456 measured in the ELISA and FP assays and those observed in the cell-based assays. Without being bound by theory, these differences may be attributed to the fact that in the cellular milieu, the uPAR-uPA complex binds to a number of cell surface receptors and other proteins, such as a number of intergrins (27), vitronectin (39. Gardsvoll & Ploug (2007) Mapping of the vitronectin-binding site on the urokinase receptor: involvement of a coherent receptor interface consisting of residues from both domain I and the flanking interdomain linker region. The Journal of biological chemistry 282(18):13561-13572) and receptor tyrosine kinases like PDGF-R (40. Kiyan et al. (2005) Urokinase-induced signaling in human vascular smooth muscle cells is mediated by PDGFR-beta. Embo J 24(10):1787-1797). It is suggested that these interactions may potentially stabilize the complex formation and increase the concentration of compound required to disrupt the complex.

It was also observed that IPR-456 appeared to lack an effect on H1299 or MDA-MB-231 tumor cell adhesion to either virtronectin or fibronectin. Without being bound by theory, it is suggested that this may be particularly noteworthy given the evidence reported over the years implicating the receptor with activation of integrins, such as $\alpha_5\beta_1$ and $\alpha_3\beta_1$, which is believed to play a critical role in adhesion (41, 42). Without being bound by theory, it is also suggested that this may not by any means suggest that uPAR does not associate and activate integrins. Instead these results may be taken to suggest that uPAR may associate to integrin through alternative interaction sites on the receptor. Two such sites have been reported to exist, namely vitronectin (39) and integrin (41. Wei et al. (2005) Regulation of alpha5beta1 integrin conformation and function by urokinase receptor binding. J Cell Biol 168(3): 501-511; 42. Wei et al. (2001) Urokinase receptors promote beta 1 integrin function through interactions with integrin alpha 3 beta 1. Molecular biology of the cell 12(10):2975-2986). In addition to serving as a lead that may be useful for the development of a therapeutic agent to block metastasis, IPR-456 may also be useful as a chemical probe to delineate the role of the uPAR•uPA interaction in various processes in metastasis. It is suggested that this compound may now make it possible to probe these interactions in vivo. It is also suggested that compounds that selectively modulate other interactions of the urokinase kinase receptor may be valuable to better understand the role of the multiple interactions of this receptor.

Example in vivo Pharmacokinetics of IPR-803 in mice. Compounds are administered to mice via a single dose of 200 mg/kg by oral gavage using a formulation of saline. Blood (20 µA) is taken from the mice at their tails at time intervals of 1, 2, 4, 6, 8 and 10 hours (three time points from each of the 18 mice (21)) post injection. Blood plasma samples are prepared by centrifugation for quantification and HPLC-MS/MS analysis. Compounds are detected in plasma reaching a maximum concentration (Cmax) of 5 µM after 1 hour (tmax) (FIG. 5). The stability of the compounds in plasma is reflected by the half-life (t1/2). To gain insight into its absorption following oral dosing, intravenous bioavailability of compounds described herein is determined. Compounds are injected intravenously (IV) into the tail vein. Blood plasma samples are prepared from collected blood samples at 5, 10, 20, 45 and 120 minutes (three mice per time point). IPR-803 was administered at 200 mg/kg p.o. to test animals, and conventional pharmacokinetic measurements were made: $C_{max}$ 2601 ng/mL; $t_{max}$ 1 h, $AUC_{0-t}$ 11276 ng/mL*h; $AUC_{0-\infty}$ 13716 ng/mL*h; $t_{1/2}$ 4.7 h; Cl/F 0.379 L/h; and $Vd_{ss}/F$ 2.23 L. Based on these data, the oral bioavailability is estimated at 4%. However, an LC/MS/MS quantification of IPR-803 in the primary tumor at 1, 2, 4, 6, and 8 hour intervals revealed the inhibitor was found at levels near 10 µM. The levels of the compound in tumor tissue remained high even after 10 hours.

Example in vivo Efficacy of IPR-803 in xenograft mice model of cancer. Breast Cancer Metastasis. The Example is performed as described in Wang et al. (2011) Virtual Screening Targeting the Urokinase Receptor, Biochemical and Cell-Based Studies, Synthesis, Pharmacokinetic Characterization, and Effect on Breast Tumor Metastasis. *J Med Chem* In press, the disclosure of which is incorporated herein in its entirety. Briefly, TMD-231 cells are inoculated into the mammary fat pad of female NOD/SCID mice. Dosing is initiated at day 15 post implantation. Animals are randomized and treated with vehicle or with test compound by daily oral gavage at a dose of 200 mg/kg. Tumor volumes are determined by caliper measurements on a twice weekly basis, and calculated according to the formula $(\alpha^2 \times \beta(3)/2$, where $\alpha$ is the shorter and $\beta$ is the longer of the two dimensions. The study is conducted over a period of 33 days. The primary tumor in both control and treated mice grew substantially over the course of the study. Tumor volumes reached nearly 693 and 785 mm³ for treated and untreated mice, respectively. The minimal effects (~10%) on tumor size are fully consistent with previous studies that have shown that uPAR is not a lethal target. In addition, these studies further support our cellular studies that have found that IPR-803 is not cytotoxic and does not have a signaling affect on pathways implicated with growth, such as ERK.

While uPAR's effects on growth are known to be minimal, its role in promoting invasion and metastasis is widely established. To assess the effect of IPR-803 on metastasis, control and experimental animals were sacrificed and organs (lungs) were removed and evaluated for the presence of tumors. The number and size of metastasis in two to five fields per sample were calculated. A score of 4+ was given to a sample with highest metastasis index and relative metastasis in other samples are calculated (i.e., 1+, 2+, 3+) by a sample-blinded pathologist. The extent of metastasis in treated versus untreated was significantly different. The extent of metastasis was significantly more severe in the untreated mice. For example, 11 out of 13 untreated mice developed severe (score=3) or marked (score=4) metastasis to the lung. This is compared to only 4 in the treated mice. Among the treated mice, 4 developed moderate metastasis, and another four were scored at 1 or lower, showing mild metastasis to the lungs.

Figure 4:
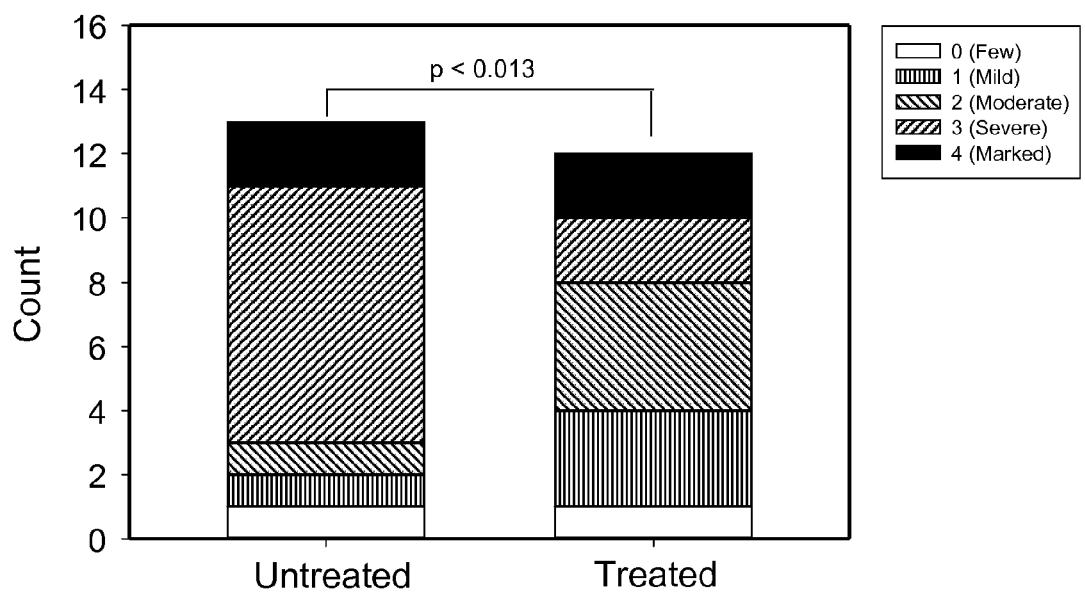
FIG. 4 shows the in vivo efficacy of IPR-803 (treated) compared to vehicle control (untreated).

IPR-803 was administered at 200 mg/kg p.o. to test animals, and conventional evaluation of cancer progression and survival measurements were made. IPR-803 exhibited statistically significant (p<0.013) improvement in outcome (n=15) compared to vehicle (n=15), as shown in FIG. 4. It is observed that there is a greater percentage of mild an moderate outcomes in the treatment group compared to the untreated group showing a majority of severe outcomes. In addition, whole animal toxicity was evaluated by periodic measurement of weight change in test animals. No significant weight change was observed in the IPR-803 treated group (n=15) compared to vehicle control (n=15)

COMPOUND EXAMPLES

Synthesis. All chemicals were purchased from commercially available sources and used as received. Column chromatography was carried out with silica gel (25-63μ). High-Res Mass Spectra were measured on an Agilent 6520 Accurate Mass Q-TOF instrument. $^1$H NMR was recorded in $CDCl_3$ or DMSO on a Bruker 500 MHz spectrometer. RP-LCMS was carried out on a Agilent 1100 LC/MSD fitted with a Eclipse XBD-C18 (4.6×150 mm) column eluting at 1.0 ml/min employing a gradient of (acetonitrile:methanol):water (each containing 5 mM $NH_4OAc$) from 70% to 100% acetonitrile:methanol over 15 min and holding at 100% acetonitrile:methanol for 2 min. Chemical shifts are reported in ppm using either residual $CHCl_3$ or DMSO as internal references.

3,5-dibromo-6H-anthra[1,9-cd]isoxazol-6-one (1)—Sodium nitrite (993 mg, 14.4 mmol) was added with stirring to conc. $H_2SO_4$ (25 mL) at 30-40° C. over 10 min then stirred for an additional 30 min. Next 1-amino-2,4-dibromoanthraquinone (5.0 g, 13.1 mmol) was added over 15 min and the mixture was stirred overnight (16 h) at 50-55° C. The heated solution was poured directly over ice and the resulting yellow precipitate was filtered, washed with cold water, and a 1:1 mixture of ethanol-ether. The moist anthraquinonediazonium hydrogensulfate was added to a solution of $NaN_3$ (1.37 g, 21.0 mmol) in water (25 mL) and stirred overnight (16 h). The light orange solid was filtered off and washed with water followed by a 9:1 mixture of acetone-water. The moist azide was suspended in toluene (40 mL) and heated to 70° C. with stirring. Water and acetone were slowly distilled (using a Dean-Stark apparatus) over a 12 h period. The yellow-orange crystals were filtered and washed with methanol to give 3.78 g (76%) of 3,5-dibromo-6H-anthra[1,9-cd]isoxazol-6-one. $^1$H NMR (500 MHz, $CDCl_3$) δ 8.44 (d, J=7.8 Hz, 1H), 8.07 (d, J=7.4 Hz, 1H), 7.97 (s, 1H), 7.80 (t, J=7.0 Hz, 1H), 7.71 (t, J=7.4 Hz, 1H). Reference: Sutter, P; Weis, C. D. *J. Heterocyclic Chem.* 1982, 19, 997-1011.

Methyl 3-((3-bromo-6-oxo-6H-anthra[1,9-cd]isoxazol-5-yl)amino)benzoate (2)—To a solution of methyl 3-aminobenzoate (481 mg, 3.18 mmol) in nitrobenzene (3 mL), anhydrous $AlCl_3$ (353 mg, 2.65 mmol) was added with vigorous stirring. After five minutes, 1 was added and the reaction mixture stirred for 3 h at ambient temperature. The reaction mixture was poured into an ice-water slurry that precipitated a reddish solid which was filtered off. The reddish solid was recrystallized from toluene to give 144 mg (61%) of 2. $^1$H NMR (500 MHz, $CDCl_3$) δ 11.40 (s, 1H), 8.55 (d, J=8 Hz, 1H), 8.15 (d, J=8 Hz, 1H), 8.07-8.01 (m, 2H), 7.81 (t, J=7.5 Hz, 1H), 7.72-7.66 (m, 2H), 7.63-7.53 (m, 2H), 3.97 (s, 3H). Reference: Nabar, U. T.; Kanetkar, V. R.; Sunthankar, S. V. *Indian J. Chem.* 1983, 22B, 812-814.

Methyl 3-((3-(azepan-1-yl)-6-oxo-6H-anthra[1,9-cd]isoxazol-5-yl)amino)benzoate (3)—Hexamethyleneimine (62 μL, 0.55 mmol) and 2 (100 mg, 0.22 mmol) were dissolved in acetonitrile (4 mL). The reaction solution was heated to 70-80° C. As determined by TLC the reaction was complete after 3 h afterwards the reaction mixture was cooled to ambient temperature then to −15° C. for 1 h. The reddish solid was filtered off and washed with cold acetonitrile to give 52 mg (50%) of 3. $^1$H NMR (500 MHz, $CDCl_3$) δ 11.94 (s, 1H), 8.63 (d, J=8 Hz, 1H), 8.19-8.14 (m, 2H), 7.91 (d, J=7 Hz, 1H), 7.73 (t, J=7 Hz, 1H), 7.64 (t, J=8 Hz, 1H), 7.58-7.50 (m, 2H), 6.18 (s, 1H), 4.51-3.40 (vbr s, 4H), 3.94 (s, 3H), 1.91 (br s, 4H), 1.65 (br s, 4H). Reference: Gornostaev, L. M.; Dolgushina, L. V.; Titova, N. G.; Arnol'd, E. V.; Lavrikova, T. I. *Russ. J. Org. Chem.* 2006, 42, 1364-1367.

3-((3-(azepan-1-yl)-6-oxo-6H-anthra[1,9-cd]isoxazol-5-yl)amino)benzoic acid (4)-3 (433 mg, 0.93 mmol) was hydrolyzed in a methanol (4 mL) and 2M aq. NaOH (2 mL) solution at 80° C. with stirring overnight. The residual methanol was removed in vacuo, and the resulting residue was acidified to pH 2. The precipitate was filtered off and washed with cold water to give 4 (314 mg, 74%) as a reddish-brown solid. $^1$H NMR (500 MHz, DMSO) δ 11.79 (s, 1H), 8.44 (app d, J=8 Hz, 1H), 8.13 (app d, J=8 Hz, 1H), 8.01 (s, 1H), 7.84-7.78 (m, 2H), 7.72-7.67 (m, 2H), 7.64-7.59 (m, 1H), 6.12 (s, 1H), 4.51-3.97 (br s, 4H), 1.80 (br s, 4H), 1.55 (br s, 4H); $^{13}$CNMR (126 MHz, DMSO) δ 174.7, 166.8, 153.6, 152.8, 147.6, 146.0, 138.5, 132.9, 132.4, 131.2, 130.2, 128.3, 127.5, 127.4, 126.0, 123.4, 121.8, 118.5, 99.5, 95.0, 91.7, 56.0, 26.0, 18.6. HRMS calc'd for $C_{27}H_{22}N_3O_4$ (M−H)$^-$ 452.1610. found 452.1601.

Sodium 3-((3-(azepan-1-yl)-6-oxo-6H-anthra[1,9-cd]isoxazol-5-yl)amino)benzoate (5)-4 (100 mg, 0.22 mmol) was slowly added to a suspension of NaH (5.3 mg, 0.22 mmol) and THF (1.5 mL). The reaction was stirred at room temperature for 1 h. THF was removed in vacuo to give 5 (103 mg, 98%) as a reddish-brown solid. ES (+) MS m/e=454 (M+H)$^+$; LCMS $t_r$=7.44 min, 97% purity. HRMS calc'd for $C_{27}H_{24}N_3O_4$ (M+H)$^+$ 454.1761. found 454.1782.

What is claimed is:

1. A method for imaging or diagnosing a population of pathogenic cells, the method comprising contacting the population with one or more compositions comprising a therapeutically effective amount of one or more compounds of the formula

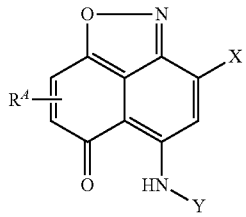

or a pharmaceutically acceptable salt thereof, wherein
X is $NH_2$, alkylamino, dialkylamino, or an optionally substituted nitrogen-containing heterocycle attached at nitrogen;
Y is optionally substituted aryl or optionally substituted heteroaryl; and
$R^4$ represents two substituents, each independently selected from the group consisting of hydrogen, halo, hydroxy, amino, thio, carboxylate, sulfinyl, sulfonyl, phosphinyl, phosphonyl, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; or $R^4$ is a fused aryl or heteroaryl, each of which is optionally substituted, and measuring a signal from the population.

2. The method of claim 1, wherein the signal is a fluorescence signal.

3. The method of claim 1, wherein the measuring step includes determining the red shift of the fluorescent signal.

4. A pharmaceutical composition comprising a therapeutically effective amount of one or more compounds of the formula

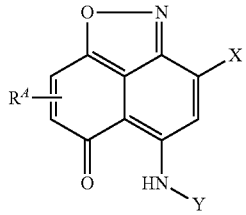

or a pharmaceutically acceptable salt thereof, wherein $R^4$ is an optionally substituted fused aryl, X is an optionally substituted nitrogen-containing heterocycle attached at nitrogen and Y is an optionally substituted aryl, such that the compound is of the formula

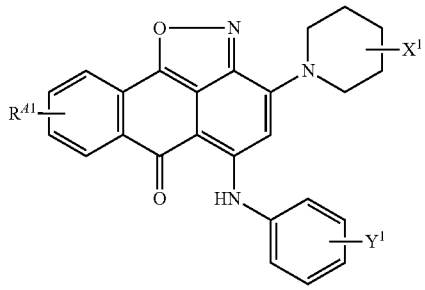

or a pharmaceutically acceptable salt thereof, wherein
$X^1$ represents five substituents, each independently selected from the group consisting of hydrogen, halo, hydroxy, amino, thio, carboxylate, sulfinyl, sulfonyl, phosphinyl, phosphonyl, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl and heteroarylalkyl, each of which is optionally substituted;
$Y^1$ represents five substituents, each independently selected from the group consisting of hydrogen, halo, hydroxy, amino, thio, carboxylate, sulfinyl, sulfonyl, phosphinyl, phosphonyl, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl and heteroarylalkyl, each of which is optionally substituted; and
$R^{41}$ represents four substituents, each independently selected from the group consisting of hydrogen, halo, hydroxy, amino, thio, carboxylate, sulfinyl, sulfonyl, phosphinyl, phosphonyl, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl and heteroarylalkyl, each of which is optionally substituted.

5. The pharmaceutical composition of claim 4, wherein, in the one or more compounds, or a pharmaceutically acceptable salt thereof, each $X^1$ is selected from hydrogen and alkyl; and each $Y^1$ is selected from hydrogen and carboxylate.

6. The pharmaceutical composition of claim 4, wherein $Y^1$ in the one or more compounds, or a pharmaceutically acceptable salt thereof, is a single carboxylate.

7. A pharmaceutical composition comprising a therapeutically effective amount of a compound of the formula

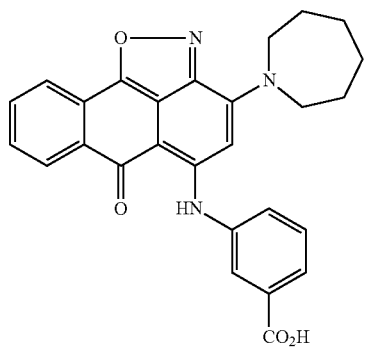

or a pharmaceutically acceptable salt thereof.

8. The pharmaceutical composition of claim 4, wherein the compound is a compound of the formula

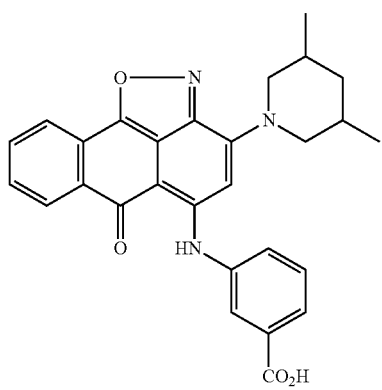

or a pharmaceutically acceptable salt thereof.

9. The pharmaceutical composition of claim 4, wherein the compound is a compound of the formula

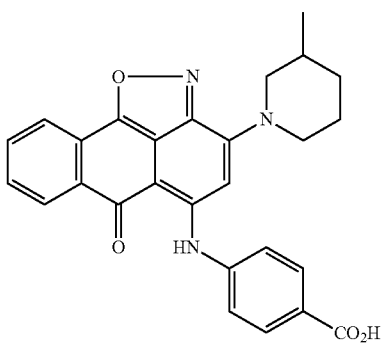

or a pharmaceutically acceptable salt thereof.

10. The pharmaceutical composition of claim 4, wherein the compound is a compound of the formula

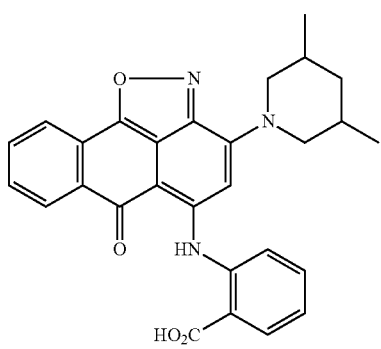

or a pharmaceutically acceptable salt thereof.

* * * * *